United States Patent [19]

Rauleder et al.

[11] Patent Number: 4,876,337

[45] Date of Patent: Oct. 24, 1989

[54] METHOD AND APPARATUS FOR THE PREPARATION OF CYANOALKYL-ALKOXYSILANES

[75] Inventors: Hartwig Rauleder; Claus-Dietrich Seiler, both of Rheinfelden; Hans-Joachim Vahlensieck, Wehr, all of Fed. Rep. of Germany

[73] Assignee: Huels Troisdorf AG, Troisdorf, Fed. Rep. of Germany

[21] Appl. No.: 278,736

[22] Filed: Dec. 2, 1988

[30] Foreign Application Priority Data

Dec. 24, 1987 [DE] Fed. Rep. of Germany ....... 3744211

[51] Int. Cl.$^4$ ................................................ C07F 7/10
[52] U.S. Cl. ..................................................... 556/415
[58] Field of Search ......................................... 556/415

[56] References Cited

U.S. PATENT DOCUMENTS

| | | | |
|---|---|---|---|
| 3,032,575 | 5/1962 | Freitag et al. | 556/415 |
| 3,330,628 | 7/1967 | Johns | 556/415 X |
| 4,328,351 | 5/1982 | Findeisen et al. | 556/415 |
| 4,429,145 | 1/1984 | Reetz et al. | 556/415 |

FOREIGN PATENT DOCUMENTS

| | | | |
|---|---|---|---|
| 0090356 | 11/1981 | European Pat. Off. | 556/415 |
| 0076413 | 4/1983 | European Pat. Off. | 556/415 |
| 0135393 | 6/1988 | Japan | 556/415 |

Primary Examiner—Paul F. Shaver
Attorney, Agent, or Firm—Felfe & Lynch

[57] ABSTRACT

In a method of preparing cyanoalkyl-akoxysilanes, which is suitable for the production of these silanes on a large technical scale, the reaction of a chloroalkyl-alkoxysilane with an alkali metal cyanide in the presence of a solvent takes place in a stirring reactor which is provided with means for loading these starting materials and with an outlet opening for the alkali metal chloride by-product, and which is connected through a bypass valve to a column with a superimposed condenser. After the reaction in the reactor has ended, first the solvent is distilled out through the column and then the main part of the cyanosilane, and then the rest of the cyanosilane is distilled out while bypassing the column. The alkali metal chloride is then removed from the reactor through a lock.

2 Claims, No Drawings

METHOD AND APPARATUS FOR THE PREPARATION OF CYANOALKYL-ALKOXYSILANES

FIELD OF THE INVENTION

This invention relates to a method of preparing cyanoalkyl-alkoxysilanes wherein a chloroalkyl-alkoxysilane is reacted with an alkali metal cyanide in the presence of a solvent, and the resulting cyanoalkyl-alkoxysilane is separated from the alkali metal chloride which forms, and from the solvent.

BACKGROUND OF THE INVENTION

West German Patent (DE-PS) No. 10 49 376 describes a method of preparing cyanoalkyl-alkoxysilanes, hereinafter also referred to as cyanosilanes, wherein a chloroalkyl-alkoxysilane is reacted with an alkali metal cyanide in the presence of a solvent at temeratures between 25° and 175° C. under anhydrous conditions. In the practice of the method, after completion of the reaction, the precipitated alkali metal chloride is first separated at room temperature, then the solvent is distilled out, and then the cyanoalkyl-alkoxysilane is distilled out.

This method of operation has the following disadvantages:

The filtering out of the alkali metal chloride must be performed at room temperature so that, after the reaction has taken place, the reaction mixture has to be cooled. When the filtration has ended the filtrate has to be reheated to separate the solvent and cyanosilane, so that this procedure calls for a great expenditure of energy when performed on a technical scale.

Furthermore, the alkali metal chloride can be completely filtered out only in the presence of diatomaceous earth, so that this method requires an additional auxiliary substance.

In addition, the filtering out of the alkali metal chloride requires a great deal of apparatus: Besides the additional filtration apparatus, two more pieces of equipment required, one for the performance of the reaction and one for the distillation of solvents and cyanosilane.

OBJECTS OF THE INVENTION

It is an object of the present invention to conduct the reaction of a chloroalkyl-alkoxysilane with an alkali metal cyanide in such a way that the alkali metal chloride which forms is separated so that there will be no need for a second heating of the reaction medium, and that very little apparatus will be needed.

Another object of the invention is the separation of the alkali metal chloride without the use of additional auxiliary substances.

Other objects and advantages of the invention will become apparent as the description thereof proceeds.

DESCRIPTION OF THE INVENTION

We have discovered that the above objects are achieved by a method for the preparation of cyanoalkyl-alkoxysilanes which comprises reacting a chloroalkyl-alkoxysilane with an alkali metal cyanide in a solvent, separating the alkali metal chloride which is produced, and distilling out the solvent and the cyanoalkyl-alkoxysilane, wherein all of the steps are performed in a single apparatus in such a manner that, after the reaction has taken place, first the solvent is distilled out of this apparatus through a column connected to the apparatus, then most of the cyanoalkyl-alkoxysilane is distilled out through the same column, and then the remainder of the cyanoalkyl-alkoxysilane is distilled off, bypassing the column, until a dry alkali metal chloride is obtained in the apparatus, which is then removed from the apparatus through a lock in conventional manner.

In accordance with the invention, the term "apparatus" is to be understood to mean a stirrer-equipped reactor with a connectable column which has a superimposed, connectable condenser. This stirring reactor must permit a uniform stirring of the solid matter throughout the entire process. Such reactors are known by those skilled in the art; for example, paddle dryers are especially suitable.

The stirring reactor is furthermore provided with openings for loading the chloroalkyl-alkoxysilane, the solvent and the alkali metal cyanide, and for the removal of the alkali metal chloride. If the chloroalkyl-alkoxysilane is liquid at room temperature, it can be loaded into the reactor together with the solvent.

The pipe system of the entire apparatus is so designed that the condenser can be connected to the stirring reactor either through the packed column or directly, and that it has additional conventional lines leading from the condenser back to the reactor and/or to the distillate receivers.

The process steps to be performed in the apparatus include the following:

1. Reaction of the starting materials alkali metal cyanide and chloroalkyl-alkoxysilane in the solvent at temperatures between 25° and 200° C., preferably in the boiling point range of the reaction mixture, to form alkali metal chloride and cyanosilane.
2. Separation of the solvent by distillation, preferably in vacuo, using the column, which is preferably a packed column.
3. Purification of the major amount of cyanosilane by column distillation.
4. Drying of the precipitated alkali metal chloride by freeing it from adhering silane by simple distillation, by-passing the column.
5. Removal of the alkali metal chloride from the reactor.

The reaction of the alkali metal cyanide with the chloroalkyl-alkoxysilane is performed in conventional manner. Sodium cyanide is preferred as the alkali metal cyanide; however, postassium cyanide or other alkali metal or alkaline earth metal cyanides can also be used.

The second starting material is a chloroalkyl-alkoxysilane of the general formula

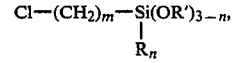

in which R is methyl or ethyl, R' is alkyl of 1 to 4 carbon atoms, m is 1 or 3 to 8, inclusive, and n is 0, 1 or 2. The preferred chloroalkyl-alkoxysilanes are 3-chloropropyl-trimethoxy- and -triethoxysilane.

Those solvents which are listed as suitable reaction media in West German Pat. No. 10 49 376 or U.S. Pat. No. 3,168,544 can also be used as solvents for the present reaction. These are solvents in which the alkali metal cyanide is at least partially soluble. It is sufficient if the alkali metal cyanide is only slightly soluble in the solvent at the selected reaction temperature. Preferably, the alkali metal chloride which forms should be less soluble in the solvent than the alkali metal cyanide.

The solvent, moreover, should have a boiling point which is lower than the boiling point of the target product.

Solvents which have this property are, for example, dialkyl-acylamides, preferably dialkyl-formamides and -acetamides. The preferred solvent is dimethylformamide.

The molar ratio of the chloroalkyl-alkoxysilane starting compound to the alkali metal cyanide starting compound should preferably be about 1:1, but the alkali metal cyanide can also be used in slight excess (up to about 10%). A large excess of alkali metal cyanide, as preferentially required in the method of West German Patent 10 49 376, is not necessary in the method of the instant invention.

The reaction temperature is generally between 100° and 200° C.. Within this range the other reaction conditions should be selected such that a liquid phase will be maintained in the reactor. This can be assured by known methods, such as, for example, by the choice of the solvent.

After the reaction has ended, first the solvent and then most of the cyanosilane are distilled out. If a stirring reactor is used, this can be accomplished without complications by the appropriate choice of the speed of the stirrer. The expression "most of the cyanosilane" is understood to mean between 80 and 95% of the cyanosilane which has formed.

After most of the cyanosilane has been distilled out, the alkali metal chloride remaining in the reactor is not yet removed but is further heated, while the gases that form are not passed through the column but fed directly into the condenser where they are condensed and captured in separate tails. These tails contain mostly cyanosilane that has additionally formed; they can be subjected to another, separate fractional distillation to increase the overall yield of the process. Preferably, the tails are collected and run together through a column still.

This "short-cut distillation" is performed until the salt remaining in the reactor is so dry that it can easily be removed. Removal is performed through a tapping valve in the bottom of the reactor, which can also be in the form of an airlock.

A stirring reactor serves as the apparatus for the reaction of the chloroalkyl-alkoxysilane with the alkali metal cyanide, preferably a paddle dryer which is provided with openings through which the starting compound and the solvent can be loaded and which has a system for removing the alkali metal chloride that is formed.

This stirring reactor is connected by a valved pipeline to a fractional distillation column which is connected to a condenser. During the first step of the process referred to above, the distillate is recycled from the condenser to the stirring reactor; during steps 2 to 4 the distillate is carried from the condenser into corresponding receivers. The pipe system between the stirring reactor, the column and the condenser must be designed accordingly, and must also make it possible for the gases issuing from the reactor to pass directly into the condenser, bypassing the column, during process step 4.

The following examples illustrate the present invention and will enable others skilled in the art to understand it more completely. It should be understood, however, that the invention is not limited solely to the particular examples given below.

EXAMPLE 1

963 g (4 mols) of 3-chloropropyl-triethoxysilane, 196 g (4 mols) of sodium cyanide and 1235 g of dimethylformamide (DMF) were loaded at room temperature into a 3-liter stirring vessel with a connectable packed column, a condenser, a connecting distillation bridge, and an apparatus for salt removal. The suspension was heated while stirring, and refluxed at about 155° C. for 10 hours.

First DMF and then 3-cyanopropyl-triethoxysilane were distilled out through the packed column at reduced pressure. In this manner 779 g of 3-cyanopropyl-triethoxysilane (84.3%) were obtained. Then, with the packed column disconnected, the already relatively dry salt was completely dried while additional volatile coponents (34 g) were distilled out through the bridge and let out of the reactor through the opening provided for that purpose. By adding this product obtained by the bridge distillation, the yield can be raised to about 87%.

The identification of the product was performed with the aid of the mass spectrum, the infrared spectrum and the nuclear resonance data ($^{13}$C-NMR and $^1$H-NMR).

EXAMPLE 2

Procedure analogous to Example 1. Starting materials: 795 g (4 mols) of 3-chloropropyl-trimethoxysilane, 196 g (4 mols) of sodium cyanide and 1200 g of DMF. Yield: 668 g (88%) of 3-cyanopropyl-trimethoxysilane.

When the product obtained by short-cut distillation was included, the yield was 89%. Mass spectrum, IR spectrum and nuclear resonance data ($^{13}$C-NMR and $^1$H-NMR) confirmed the product as 3-cyanopropyl-trimethoxysilane.

While the present invention has been illustrated with the aid of certain specific embodiments thereof, it will be readily apparent to others skilled in the art that the invention is not limited to these particular embodiments, and that various changes and modifications may be without departing from the spirit of the invention or the scope of the appended claims.

We claim:

1. In a method of preparing a cyanoalkyl-akoxysilane by reacting a chloroalkyl-akoxysilane with an alkali cyanide or an alkaline earth metal cyanide in a solvent, separating the alkali metal chloride thus produced and removing the solvent and the cyanoalkyl-akoxysilane by distillation, the improvement of performing all of the process steps in a single apparatus and, after the reaction is performed, first distilling the solvent out of the apparatus through a column connected thereto, then distilling most of the cyanoalky-alkoxysilane out of the apparatus through the same column and subsequently the rest of the cyanoalkyl-akoxysilane while bypassing the column, until a dry alkali metal chloride or alkaline earth metal chloride is obtained in the apparatus, and removing the dry chloride from the apparatus through a lock.

2. The method of claim 1, where the chloroalkyl-alkoxysilane and the alkali metal cyanide are used in equimolar amounts.

* * * * *